US 6,613,218 B1

(12) United States Patent
Chun

(10) Patent No.: US 6,613,218 B1
(45) Date of Patent: Sep. 2, 2003

(54) METHODS FOR ESTIMATING ADSORPTION ISOTHERMS IN ELECTROCHEMICAL SYSTEMS

(75) Inventor: Jang-Ho Chun, Seoul (KR)

(73) Assignee: Mission Telecom, Co., Ltd., Seoul (KR)

( * ) Notice: Subject to any disclaimer, the term of this patent is extended or adjusted under 35 U.S.C. 154(b) by 0 days.

(21) Appl. No.: 09/568,462

(22) Filed: May 10, 2000

(51) Int. Cl.[7] .............................................. G01N 27/26
(52) U.S. Cl. .................. 205/775; 205/790.5; 205/794.5
(58) Field of Search ................................. 204/400, 402, 204/434; 205/775, 790.5, 791, 793.5, 794.5

(56) References Cited

U.S. PATENT DOCUMENTS 5,656,388 A * 8/1997 Bugga et al. .................. 429/40

OTHER PUBLICATIONS

Translation of Chun et al, Journal of the Korean Electrochemical Society, 3(1), 2000, pp. 25–30.*
Chun et al, Journal of the Korean Electrochemical Society, 3(2), 2000, pp. 109–114.*
Translation of Chun et al, Journal of the Korean Electrochemical Society, 2(1), 1999, pp. 23–36.*
Chun et al., J. Korean Electrochem. Soc., vol. 3, No. 1, pp. 25–30, 2000, month unavailable.*
Chun et al., J. Korean Electrochem. Soc., vol. 2, No. 1, pp. 23–26, 1999, month unavailable.*
CAS Abstract for Chun et al., J. Korean Electrochem. Soc., vol. 3, No. 2, pp. 109–114, 2000, month unavailable.*
Bard and Faulkner, "Electrochemical Methods: Fundamentals and Applications", John Wiley & Sons, pp. 515, 538–540, 1980, month unavailable.*
Jang H. Chun et al., The Phase–Shift Method for the Frumkin Adsorption Isotherms at the $Pd/H_2SO_4$ and KOH Solution Interfaces, Nov. 1998, pps. 3794–3797, J. Electrochem. Soc., vol. 145, No. 11.

* cited by examiner

Primary Examiner—Nam Nguyen
Assistant Examiner—Kaj K. Olsen
(74) Attorney, Agent, or Firm—Fleshner & Kim, LLP

(57) ABSTRACT

The present invention provides a technique for enhancing electrocatalysis in electrochemical systems. Electrochemical impedance spectroscopy is performed for an electrode/electrolyte system at an intermediate frequency. Using an appropriate equivalent circuit model, the corresponding phase-shift can be derived. From this data, the Langmuir absorption isotherm can be created to determine the relation of and transition between overpotentially deposited and underpotentially deposited reactive species. Knowledge of the overpotentially and underpotentially deposited reactive species permits optimal selection of the operating conditions for an electrochemical system.

15 Claims, 8 Drawing Sheets

METHODS FOR ESTIMATING ADSORPTION ISOTHERMS IN ELECTROCHEMICAL SYSTEMS

BACKGROUND OF THE INVENTION

1. Field of the Invention

The present invention relates to electrode kinetics in electrochemical systems and, in particular, to techniques for improving electrode electrocatalysis in such systems. More particularly, the invention relates to the application of an electrochemical impedance spectroscopic method for determining the Langmuir or the Frumkin adsorption isotherms.

2. Background of the Related Art

Adsorption of a reactive species on an electrode surface has important consequences in an electrochemical system. Adsorption may hinder the electrode reaction by forming a blocking layer on the electrode surface; alternatively, adsorption may enhance reactivity of an electrochemical system by increasing the reactivity of the adsorbed species through dissociation of a nonreactive material into reactive species. In the latter situation, the electrode functions as a catalyst for a reduction or oxidation reaction, a process termed "electrocatalysis." The relationship among the amount of a particular species adsorbed on an electrode, the activity of the species in bulk solution, and the electrical state of the electrochemical system at a particular temperature is given by the adsorption isotherm. The relationship among the fractional electrode surface coverage of these species and the electrode kinetic parameters is described by the Langmuir and Frumkin adsorption isotherms. From the shape of the adsorption isotherms, the adsorption behavior can be interpreted. By examining the adsorption behavior of a reactive species, the optimal operating conditions for an electrochemical cell (e.g, operating potential, electrolyte concentration, electrode material/electrolyte composition combinations etc.) can be determined.

In the adsorption of ions on a dissimilar electrode material, the adsorbed species will be either more weakly adsorbed to the substrate than to a material of the same type or the adsorbed species will be more strongly adsorbed to the substrate than to a material of the same type. Species more strongly adsorbed to the dissimilar substrate are said to be underpotentially deposited, that is, they are deposited at potentials which are more positive than the equilibrium potential for deposition on a material of the same type. In underpotential deposition, the adsorbed species attempts to form a monolayer on the electrode surface.

Commercially important electrochemical systems frequently involve noble metal electrodes in acidic or alkaline aqueous solutions. In such systems, reduction of hydrogen ions at the cathode yields $H_2$. The transition between the underpotentially deposited hydrogen and the overpotentially deposited hydrogen is important to understand the mechanisms of the $H_2$ evolution reaction at the cathode.

Voltammetric and spectroscopic techniques have been used to study the adsorption processes of the underpotentially deposited hydrogen and the overpotentially deposited hydrogen on noble metal surfaces. In general, the underpotentially deposited hydrogen and the overpotentially deposited hydrogen occupy different surface adsorption sites and act as two distinguishable electroadsorbed hydrogen species. However, in the past the relation, transition, and criterion between the underpotentially deposited hydrogen and the overpotentially deposited hydrogen at the noble metal/aqueous electrolyte interfaces have been studied from the point of view of the hydrogen evolution reaction rather than focusing on the hydrogen adsorption sites and processes.

Although the Langmuir adsorption isotherm is regarded as a classical law in physical electrochemistry, it is useful and important for interpreting the relation, transition, and criterion between the underpotentially deposited hydrogen and the overpotentially deposited hydrogen and the two distinct adsorption sites for the cathodic $H_2$ evolution reaction at the interfaces.

Thus, there is a need in the art for a fast, simple, and reliable technique to characterize the relation of and the transition between underpotentially deposited hydrogen and overpotentially deposited hydrogen at electrode hydrogen adsorption sites in electrochemical systems. Knowledge of this transition region would facilitate selection of the optimal operating conditions for an electrochemical system, in particular, the enhancement of electrocatalysis at an electrode, yielding electrochemical systems of maximum performance.

SUMMARY OF THE INVENTION

By the present invention, measurement techniques yield the Langmuir adsorption isotherms from which the transition region between underpotentially deposited hydrogen and overpotentially deposited hydrogen at an electrochemical system electrode is ascertained. According to the present invention, an electrochemical impedance spectroscopic method creates a phase-shift profile for the intermediate frequencies which can be used to determine the Langmuir or the Frumkin adsorption isotherm. The phase-shift method is convenient and useful for studying the electrode kinetics related to the Langmuir adsorption isotherm, the relation and transition between the underpotentially deposited hydrogen and the overpotentially deposited hydrogen, and the two distinct adsorption sites for the cathodic hydrogen evolution reaction at electrode/electrolyte interfaces. This method demonstrates that the criterion of the underpotentially deposited hydrogen and the overpotentially deposited hydrogen is the hydrogen adsorption sites and processes rather than the hydrogen evolution reaction, facilitating the study of intermediate adsorption processes in electrode kinetics. The technique of the present invention permits selection of the desired operating parameters for an electrode/electrolyte system thereby increasing electrode electrocatalysis and creating more efficient electrochemical systems.

DETAILED DESCRIPTION OF PREFERRED EMBODIMENTS

According to the present invention, the phase-shift profile for intermediate frequencies from an electrochemical impedance spectroscopic method can be used to determine the Langmuir or the Frumkin adsorption isotherm. The phase-shift method is convenient and useful for studying the electrode kinetics related to the Langmuir adsorption isotherm, the relation and transition between the underpotentially deposited hydrogen and the overpotentially deposited hydrogen, and the two distinct adsorption sites for the cathodic $H_2$ evolution reaction at electrode/electrolyte interfaces. In surface electrochemistry, a phase shift is attributed to an interfacial capacitance which consists of a parallel connection of a double-layer capacitance and a pseudocapacitance. The double layer capacitance and the pseudocapacitance depend on the electrode potential and the fractional surface coverage with the electrode potential. These features can be determined through appropriate modeling of measured spectroscopic data, thus providing the relation of and transition between underpotentially and overpotentially deposited reactive species.

Initially, electrochemical impedance spectroscopy is performed for a selected electrode/electrolyte system. In electrochemical impedance spectroscopy, a sinusoidally varying potential with a small amplitude is applied to an electrode/electrolyte interface; the current response of the system is measured. The applied modulation frequency is varied through a large range of frequencies. Through plotting the frequency response curves (|Z| vs. f where Z represents the impedance) for an electrode/electrolyte system, the intermediate frequencies are determined as the center frequencies of the slope portions (i.e., a slope of −1). Because various electrode processes affect the impedance in different ways, impedance spectroscopy can yield useful information about electrode kinetics.

Figure 3:
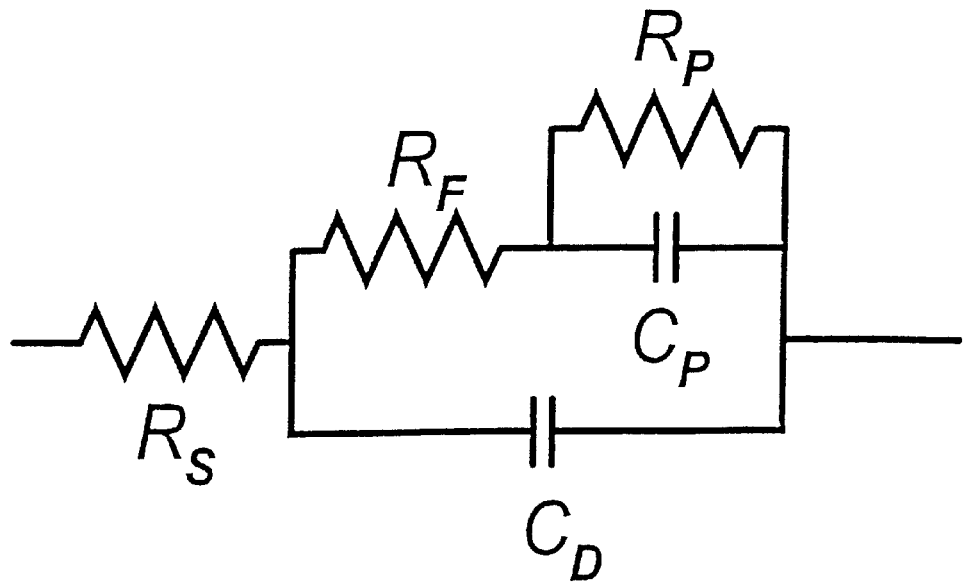
FIG. 3 is an equivalent circuit for the cathodic $H_2$ evolution reaction at the poly-Ir/0.1 M KOH and 0.1 M $H_2SO_4$ electrolyte interfaces.

An equivalent circuit is used to model the impedance of the measured electrochemical system using circuit elements such as capacitors and resistors. For a cathodic H2 evolution reaction, a typical equivalent circuit is depicted in FIG. 3. In FIG. 3, $R_S$ is the electrolyte resistance, $R_F$ is the faradaic resistance for the discharge reaction, $R_P$ is the faradaic resistance for the recombination reaction, $C_P$ is the equivalent circuit element of the adsorption pseudocapacitance, and $C_D$ is the double-layer capacitance. At low frequencies, the equivalent circuit can be expressed as a serial connection of $R_S$, $R_F$, and $R_P$. At high frequencies, the equivalent circuit can be expressed as a serial connection of $R_S$ and $C_D$. At intermediate frequencies, it has been determined that the equivalent circuit of FIG. 4 can be applied to model the frequency response of the interface.

Figure 4:
FIG. 4 is a simplified equivalent circuit for the intermediate frequencies at the poly-Ir/0.1 M KOH and 0.1 M $H_2SO_4$ electrolyte interfaces.

Using the equivalent circuit of FIG. 4, a table is constructed from the impedance spectroscopy measurements at the intermediate frequencies, listing values for each of the equivalent circuit elements. A table constructed for the equivalent circuit of FIG. 4 is shown below in connection with the Examples.

From the simplified equivalent circuit for the intermediate frequencies shown in FIG. 4, the corresponding phase shift or angle can be derived as Equation [1]

$$\phi = -\tan^{-1}[1/\omega(R_S+R_F)C_P] \quad [1]$$

$$C_P \cong C_\phi \text{ or } C_\phi \quad [2]$$

$$C_\phi = \gamma(d\theta/dE) \quad [3]$$

where $\omega(=2\pi f)$ is the angular frequency, $C_\phi$ is the adsorption pseudocapacitance for the Langmuir adsorption condition, $\gamma$ is the charge corresponding to the saturation coverage of $\theta$, $\theta$ is the fractional surface coverage of H adsorption, and E is the cathode potential. A minus sign shown in Equation [1] implies a lagged phase. From Tables 1, 2 (see Example), and Equation [1], it is readily understood that $\phi$ definitely depends on $C_P$, i.e., $C_\phi$ or $\theta$.

From the measured values for the equivalent circuit elements and the derived phase-shift determined above, the Langmuir adsorption isotherm can be constructed. The Langmuir adsorption isotherm is based on the assumptions that the surface is homogeneous and that lateral interaction effects are negligible. Considering the application of the Langmuir adsorption isotherm to the formation of H on the poly-Ir surface, the Langmuir adsorption isotherm can be expressed as follows:

$$[\theta/(1-\theta)] = KC_{H+}[\exp(-EF/RT)] \quad [4]$$

where $\theta$ is the fractional surface coverage of H adsorption, K is the equilibrium constant for H adsorption, $C_{H+}$ is the $H^+$ concentration in the bulk electrolyte, E is the cathode potential, F is the Faraday constant, R is the gas constant, and T is the absolute temperature.

The Langmuir adsorption isotherm demonstrates the relation and transition between underpotentially deposited and overpotentially deposited hydrogen as well as the electrode kinetic parameters.

The above-described process is demonstrated below for hydrogen adsorption on polycrystalline iridium electrodes.

EXAMPLE 1

A. Cyclic Voltammetric and A.C. Impedance Scans for Polycrystalline Iridium/0.1 M KOH and Polycrystalline Iridium/0.1 M $H_2SO_4$ Interfaces Taking into account $H^+$ concentrations and effects of pH, alkaline and acidic aqueous electrolytes were prepared from KOH (Alfa Aesar, Johnson Matthey, purity: 99.995%) and $H_2SO_4$ (Matsunoen, special grade) with purified water (resistivity: >18 MΩcm) obtained from a Millipore system. The 0.1 M KOH and 0.1 M $H_2SO_4$ aqueous electrolytes were de-aerated with 99.999% purified nitrogen gas for 20 min before the experiments.

A standard 3-electrode configuration was employed using an SCE reference electrode and an Ir wire (Johnson Matthey, purity: 99.8%, 1 mm diameter, surface area: 1.01 $cm^2$) working electrode. A Pt wire (Johnson Matthey, purity: 99.95%, 1.5 min diameter, surface area: 1.03 $cm^2$) was used as a counter electrode. To prepare homogeneous surfaces, both the Ir and Pt electrodes were cleaned by flame annealing and then quenched in the Millipore Milli-Q water. X-ray diffraction (XRD) analysis for the Ir working electrode was performed using a Rigaku x-ray diffractometer. The prepared Ir working electrode was polycrystalline.

The Ir working and Pt counter electrodes were separately placed (~4 cm) in the same compartment Pyrex cell using Teflon holders. The Ir working electrode was pretreated using a cyclic voltammetric method (scan potential: 0 to −0.98 V vs. SCE, scan rate: 40 mV/s for the 0.1 M KOH electrolyte and scan potential: 0 to −0.27 V vs. SCE, scan rate: 30 mV/s for the 0.1 M $H_2SO_4$ electrolyte). After pretreating (fifth scan), an ac impedance technique (scan frequency: $10^4$ to 1 Hz, ac amplitude: 5 mV, dc potential: −0.40 to −1.20 V vs. SCE for the 0.1 M KOH electrolyte and scan frequency: $10^4$ to 0.1 Hz, ac amplitude: 5 mV, dc potential: −0.05 to −0.50 V vs. SCE for the 0.1 M $H_2SO_4$ electrolyte) was used to study the relation between the phase-shift profiles for the intermediate frequencies and the Langmuir adsorption isotherms.

The cyclic voltammetric experiment was performed using an EG&G PAR Model 273A potentiostat controlled with the PAR Model 270 software package. The ac impedance experiment was performed using the same apparatus in conjunction with a Schlumberger SI 1255 HF Frequency Response Analyzer controlled with the PAR Model 388 software package. In order to obtain comparable and reproducible results, all measurements were carried out using the same preparations, procedures and conditions at room temperature. The international sign convention is used, i.e., cathodic currents and lagged phase shifts or angles are taken as negative.

Figure 1:
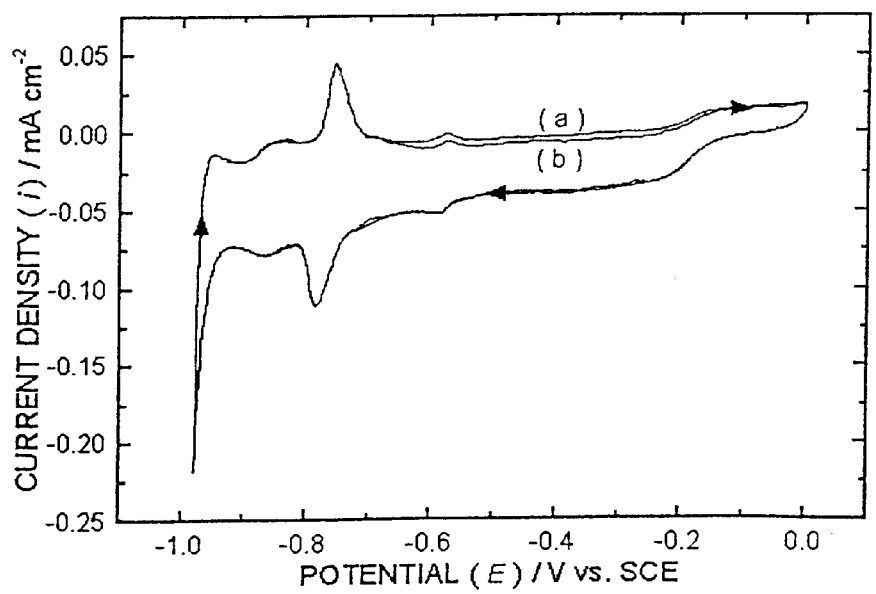
FIG. 1 depicts cyclic voltammograms at the polycrystalline iridium/0.1 M KOH electrolyte interface using a scan potential of 0 to −0.98 V vs. SCE and a scan rate of 40 mV/s in which the curve marked (a) represents the fourth scan and the curve marked (b) represents the fifth scan.

FIG. 1 shows the typical cyclic voltammograms at the poly-Ir/0.1 M KOH electrolyte interface. At the forward scan (0 to −0.98 V vs. SCE), the cathodic peak occurs at ca. −0.78 V vs. SCE. At the backward scan (−0.98 to 0 V vs. SCE), the anodic peak occurs at ca. −0.75 V vs. SCE. The cathodic and anodic peaks are the hydrogen adsorption and desorption peaks, respectively. Both the cathodic and anodic peaks on the cyclic voltammogram are attributed to the underpotentially deposited hydrogen.

Figure 2:
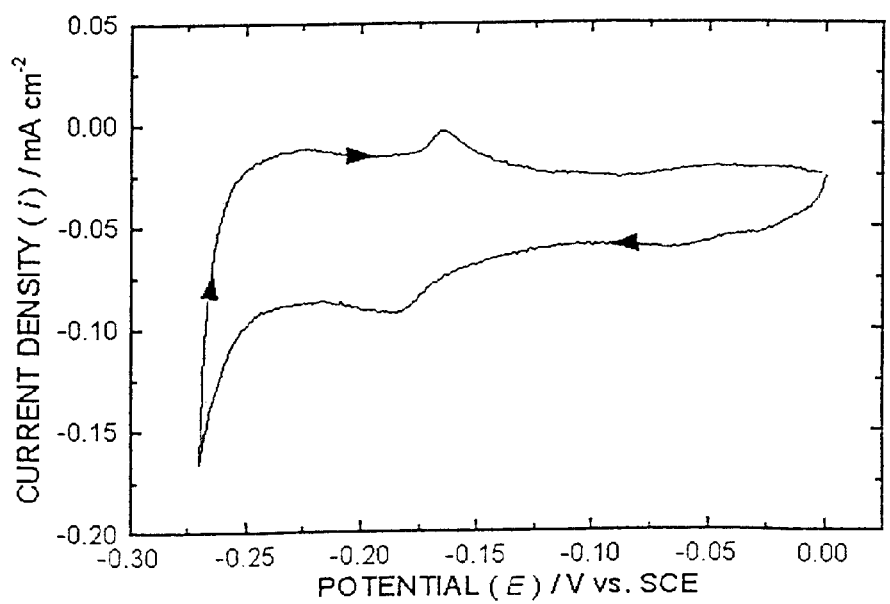
FIG. 2 is a cyclic voltammogram (fifth scan) at the polycrystalline iridium/0.1 M $H_2SO_4$ electrolyte interface. Scan potential: 0 to −0.27 V vs. SCE. Scan rate: 30 mV/s.

FIG. 2 shows the typical cyclic voltammogram (fifth scan) at the poly-Ir/0.1 M $H_2SO_4$ electrolyte interface. At the forward scan (0 to −0.27 V vs. SCE), the cathodic peak occurs at ca. −0.185 V vs. SCE. At the backward scan (−0.27 to 0 V vs. SCE), the anodic peak occurs at ca. −0.166 V vs. SCE. The cathodic and anodic peaks are the hydrogen adsorption and desorption peaks, respectively. Both the cathodic and anodic peaks on the cyclic voltammogram are attributed to the underpotentially deposited hydrogen. The anionic adsorption effect on the underpotentially deposited hydrogen peak has not been considered.

B. Simplified Equivalent Circuit for Intermediate Frequencies

At intermediate frequencies, the equivalent circuit of FIG. 4 can be applied to the poly-Ir/0.1 M KOH and 0.1 M $H_2SO_4$ electrolyte interfaces regardless of $H_2$ evolution. In other words, it is valid for analyzing both the underpotentially deposited hydrogen and the overpotentially deposited hydrogen at the interfaces.

Tables 1 and 2 show the measured values of the equivalent circuit elements for the intermediate frequencies at the poly-Ir/0.1 M KOH and 0.1 M $H_2SO_4$ electrolyte interfaces, respectively. As expected, the measured values of $C_P$ significantly increase with the increase of E.

TABLE 1

| E (V vs. SCE) | $R_S + R_F$ (Ω) | $C_P$ ($\mu F/cm^2$) | $R_S^*$ (Ω) | $C_D^*$ ($\mu F/cm^2$) |
|---|---|---|---|---|
| −0.650 | 31.00 | $1.694 \times 10^2$ | 6.259 | 58.21 |
| −0.700 | 41.40 | $1.842 \times 10^2$ | 6.253 | 51.35 |
| −0.750$^{TR}$ | 45.91 | $3.420 \times 10^2$ | 6.239 | 41.24 |
| −0.800$^{TR}$ | 29.12 | $4.640 \times 10^2$ | 6.260 | 33.29 |
| −0.850$^{TR}$ | 21.94 | $6.072 \times 10^2$ | 6.239 | 29.11 |
| −0.900$^{TR}$ | 21.52 | $5.643 \times 10^2$ | 6.252 | 26.70 |
| −0.950 | 26.45 | $6.103 \times 10^2$ | 6.294 | 24.63 |
| −0.975 | 30.77 | $1.205 \times 10^3$ | 6.242 | 23.77 |
| −1.000 | 25.65 | $5.564 \times 10^3$ | 6.267 | 23.04 |
| −1.050 | 23.83 | $2.970 \times 10^4$ | 6.264 | 21.94 |
| −1.100 | 24.82 | $4.135 \times 10^4$ | 6.286 | 21.76 |
| −1.150 | 23.48 | $5.805 \times 10^4$ | 6.323 | 21.78 |

$^{TR}$Transition region between the UPD H and the OPD H.
*Measured with stirring at the high frequency (ca. 8 kHz).

TABLE 2

| E (V vs. SCE) | $R_S + R_F$ (Ω) | $C_P$ ($\mu F/cm^2$) | $R_S^*$ (Ω) | $C_D^*$ ($\mu F/cm^2$) |
|---|---|---|---|---|
| −0.200 | 17.86 | $1.802 \times 10^3$ | 2.984 | 54.28 |
| −0.225 | 20.46 | $1.785 \times 10^3$ | 2.987 | 55.32 |
| −0.250 | 30.48 | $1.840 \times 10^3$ | 2.989 | 55.77 |
| −0.275 | 30.06 | $4.446 \times 10^3$ | 2.982 | 54.59 |
| −0.300 | 9.979 | $2.643 \times 10^4$ | 2.993 | 52.90 |
| −0.325 | 5.023 | $1.410 \times 10^5$ | 2.996 | 50.76 |
| −0.350 | 4.395 | $4.313 \times 10^5$ | 2.981 | 49.64 |
| −0.375 | 4.340 | $7.841 \times 10^5$ | 3.004 | 46.95 |
| −0.400 | 4.306 | $1.857 \times 10^6$ | 3.024 | 44.10 |
| −0.425 | 4.650 | $2.000 \times 10^6$ | 3.059 | 40.23 |
| −0.450 | 4.636 | $2.250 \times 10^6$ | 3.100 | 36.55 |
| −0.475 | 4.771 | $2.418 \times 10^6$ | 3.157 | 34.08 |

*Measured with stirring at the high frequency (ca. 8 kHz).

C. Phase-shift Profiles for Intermediate Frequencies

Using Equation 1, the phase shift (−φ) is determined for the intermediate frequency (about 8 Hz) at the poly-Ir/0.1 M KOH electrolyte interface and the results listed in Table 3. Similarly, results for the phase shift for the intermediate frequency (about 1 Hz) at the poly-Ir/0.1 M H$_2$SO$_4$ electrolyte interface are listed in Table 4.

TABLE 3

| E (V vs. SCE) | −φ (deg) | −φ* (deg) | θ** |
|---|---|---|---|
| −0.650 | 75.3 | 75.2 | ≈0 |
| −0.700 | 69.2 | 69.0 | 0.081 |
| −0.750$^{TR}$ | 51.9 | 51.7 | 0.310 |
| −0.800$^{TR}$ | 56.0 | 55.8 | 0.256 |
| −0.850$^{TR}$ | 56.4 | 56.2 | 0.250 |
| −0.900$^{TR}$ | 58.8 | 58.6 | 0.219 |
| −0.950 | 51.1 | 50.9 | 0.321 |
| −0.975 | 28.4 | 28.2 | 0.622 |
| −1.000 | 8.0 | 7.9 | 0.893 |
| −1.050 | 1.6 | 1.6 | 0.978 |
| −1.100 | 1.1 | 1.1 | 0.985 |
| −1.150 | 0.8 | 0.8 | ≈1 |

$^{TR}$Transition region between the UPD H and the OPD H.
*Calculated using Equation [1].
**Estimated using the measured phase shift (−φ).

TABLE 4

| E (V vs. SCE) | −φ (deg) | −φ* (deg) | θ** |
|---|---|---|---|
| −0.200 | 78.6 | 78.6 | ≈0 |
| −0.225 | 77.1 | 77.1 | 0.019 |
| −0.250 | 70.6 | 70.6 | 0.103 |
| −0.275 | 50.0 | 50.0 | 0.368 |
| −0.300 | 31.1 | 31.1 | 0.611 |
| −0.325 | 12.7 | 12.7 | 0.847 |
| −0.350 | 4.8 | 4.8 | 0.949 |
| −0.375 | 2.8 | 2.8 | 0.974 |
| −0.400 | 1.1 | 1.1 | 0.996 |
| −0.425 | 1.0 | 1.0 | 0.997 |
| −0.450 | 0.9 | 0.9 | 0.999 |
| −0.475 | 0.8 | 0.8 | ≈1 |

*Calculated using Equation [1].
**Estimated using the measured phase shift (−φ).

Tables 3 and 4 also show the comparisons of the measured and calculated phase shifts or angles at the poly-Ir/0.1 M KOH and 0.1 M H$_2$SO$_4$ electrolyte interfaces, respectively. From Tables 3 and 4, it is understood that the simplified equivalent circuit for the intermediate frequencies shown in FIG. 4 and the corresponding phase-shift equation (Equation [1]) are correctly fitted to the interfaces regardless of H$_2$ evolution.

Figure 5:
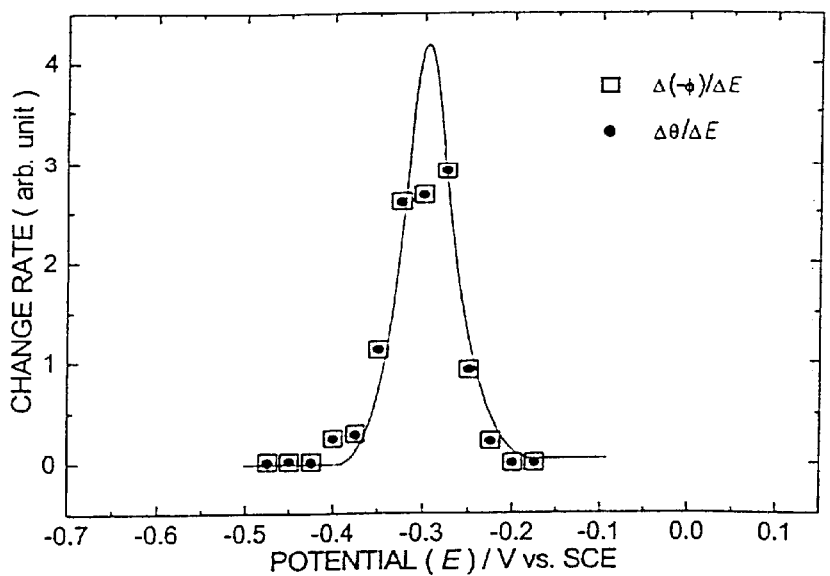
FIG. 5 is a comparison of the change rates of the $\Delta(-\phi)/\Delta E$ and the $\Delta\theta/\Delta E$ at the poly-Ir/0.1 M $H_2SO_4$ electrolyte interface.

FIG. 5 shows the comparison of the change rates of the −φ vs. E and the θ vs. E, i.e., the Δ(−φ)/ΔE or d(−φ)/dE and the Δθ/ΔE or dθ/dE, at the poly-Ir/0.1 M H$_2$SO$_4$ electrolyte interface. The derivation of the Δ(−φ)/ΔE and the Δθ/ΔE is based on the experimental data shown in Table 4. It should be noted that the Δ(−φ)/ΔE or d(−φ)/dE corresponds well to the Δθ/ΔE or dθ/dE. In other words, the shape of the change rates is exactly same as that of the adsorption pseudocapacitance (C$_φ$) for the Langmuir adsorption condition. It implies that φ or C$_P$ described in Equation [1] strongly depends on C$_φ$ or θ. Consequently, it can be seen that the phase-shift profile (−φ vs. E) for the intermediate frequencies can be related to the Langmuir adsorption isotherm (θ vs. E) at the interfaces regardless of H$_2$ evolution. The criterion of the underpotentially deposited hydrogen and the overpotentially deposited hydrogen is the H adsorption sites and processes rather than the H$_2$ evolution reaction.

Figure 6:
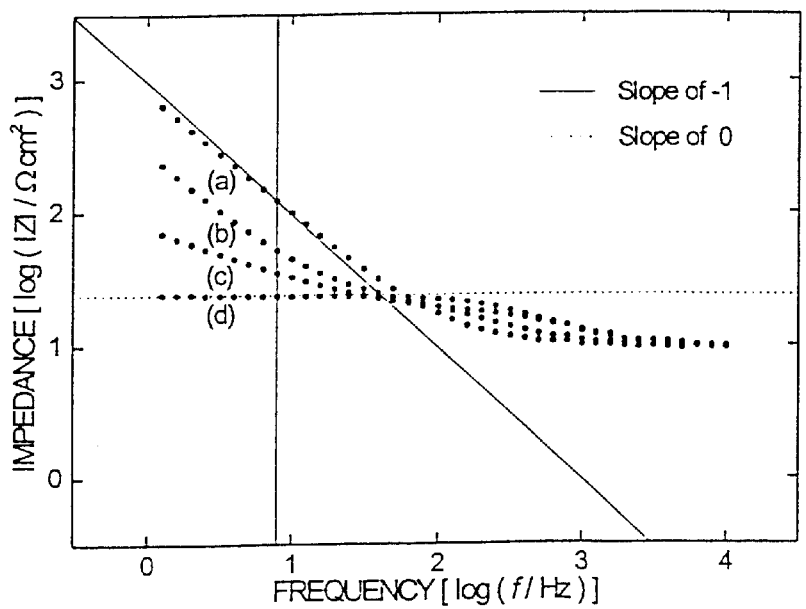
FIG. 6 shows frequency response curves (|Z| vs. f) at the poly-Ir/0.1 M KOH electrolyte interface. Single sine wave. Scan frequency: $10^4$ to 1 Hz. ac amplitude: 5 mV. dc potential: (a) 0.650 V, (b) 0.800 V, (c) 0.975V, and (d) 1.150 V vs. SCE.
Figure 7:
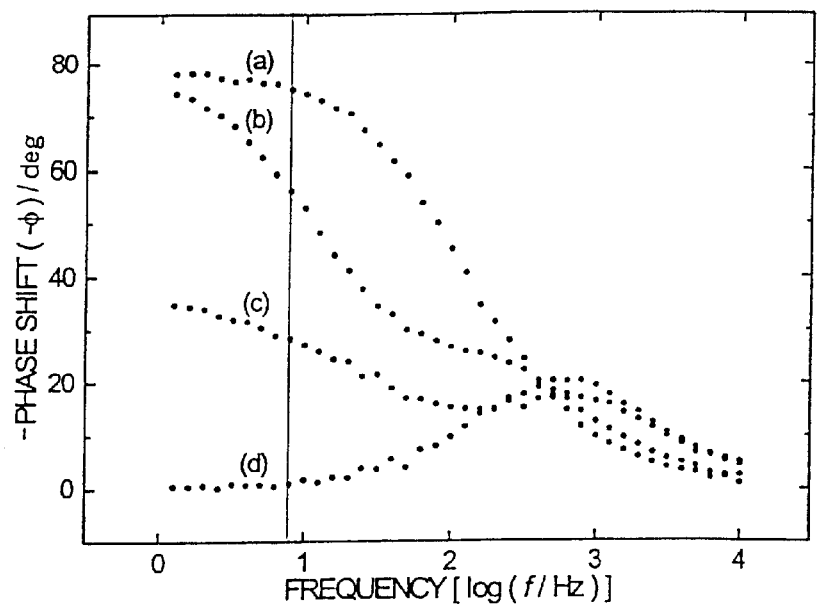
FIG. 7 depicts phase-shift curves ($-\phi$ vs. at the poly-Ir/0.1 M KOH electrolyte interface. Single sine wave. Scan frequency: $10^4$ to 1 Hz. ac amplitude: 5 mV. dc potential: (a) −0.650 V, (b) −0.800 V, (c) −0.975 V, and (d) −1.150 V vs. SCE.

FIGS. 6 and 7 show the frequency responses and the corresponding phase shifts, i.e., the Bode plots, at the poly-Ir/0.1 M KOH electrolyte interface, respectively. In FIG. 6, the absolute value of the impedance vs. the frequency (|Z| vs. f) is plotted on a log-log scale. However, it should be noted that the frequency responses and the corresponding phase shifts at the interface are markedly characterized at the intermediate frequencies, i.e., ca. 1–50 Hz. The vertical solid lines (ca. 8 Hz) shown in FIGS. 6 and 7 indicate the center frequency of the slope portion of the frequency response curve shown in FIG. 6, i.e., the optimum intermediate frequency for the phase-shift profile.

Figure 8:
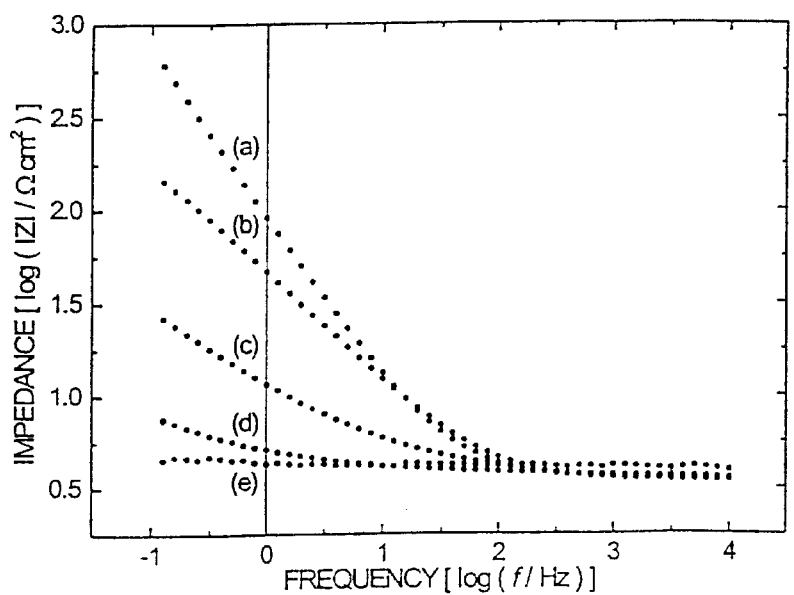
FIG. 8 depicts frequency response curves (|Z| vs. f) at the poly-Ir/0.1 M $H_2SO_4$ electrolyte interface. Single sine wave. Scan frequency: $10^4$ to 0.1 Hz. ac amplitude: 5 mV. dc potential: (a) −0.225 V, (b) −0.275 V, (c) −0.300 V, (d) −0.325 V, and (e) −0.400 V vs. SCE.
Figure 9:
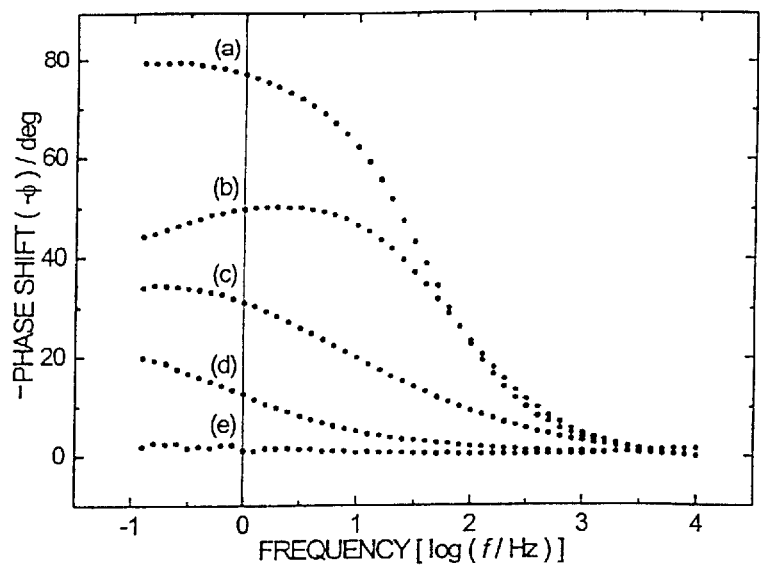
FIG. 9 depicts phase-shift curves ($-\phi$ vs. f) at the poly-Ir/0.1 M $H_2SO_4$ electrolyte interface. Single sine wave. Scan frequency: $10^4$ to 0.1 Hz. ac amplitude: 5 mV. dc potential: (a) −0.225 V, (b) −0.275 V, (c) −0.300 V, (d) −0.325 V, and (e) −0.400 V vs. SCE.
Figure 10:
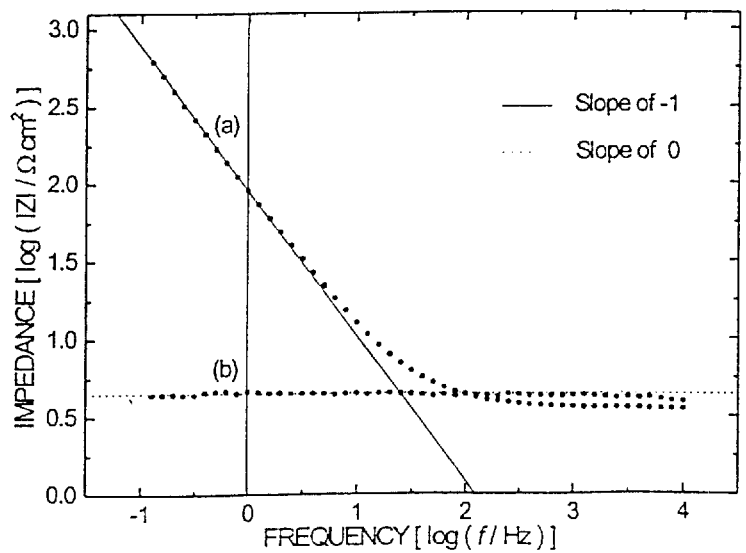
FIG. 10 is a comparison of the two extremely distinguishable frequency response curves at the poly-Ir/0.1 M $H_2SO_4$ electrolyte interface. Single sine wave. Scan frequency: $10^4$ to 0.1 Hz. ac amplitude: 5 mV. dc potential: (a) −0.200 V and (b) −0.450 V vs. SCE.

Similarly, FIGS. 8 and 9 show the frequency responses and the corresponding phase shifts at the poly-Ir/0.1 M H$_2$SO$_4$ electrolyte interface, respectively. As previously described, it should be noted that the frequency responses and the corresponding phase shifts at the interface are markedly characterized at the intermediate frequencies, i.e., ca. 0.1–10 Hz. The vertical solid lines (ca. 1 Hz) shown in FIGS. 8 and 9 indicate the optimum intermediate frequency for the phase-shift profile. FIG. 10 shows the comparison of the two extremely distinguishable frequency responses at the poly-Ir/0.1 M H$_2$SO$_4$ electrolyte interface.

In FIGS. 6(a) and 10(a), the slope portions of the frequency response curves represent capacitive behaviors of the poly-Ir/0.1 M KOH and 0.1 M H$_2$SO$_4$ electrolyte interfaces, respectively. Since a slope of −1 represents the ideal capacitive behavior, it implies that C$_P$ has a minimum value as shown in Tables 1 and 2. It also implies that θ can be set zero as shown in Tables 3 and 4. Therefore, from Equation [1], −φ has a maximum value (<90°) as shown in FIGS. 7(a) and 9(a) or Tables 3 and 4.

On the other hand, in FIGS. 6(d) and 10(b), the horizontal portions of the frequency response curves represent resistive behaviors of the poly-Ir/0.1 M KOH and 0.1 M H$_2$SO$_4$ electrolyte interfaces, respectively. Since a slope of zero represents the ideal resistive behavior, it implies that H adsorption at the interfaces is almost saturated. In other words, C$_P$ has a maximum value as shown in Tables 1 and 2. It implies that θ can be set to unity as shown in Tables 3 and 4. C$_P$ should not be confused with C$_φ$ which can be neglected at θ≈0 or 1. Therefore, from Equation [1], −φ has a minimum value (>0°) as shown in FIGS. 7(d) and 9(e) or Tables 3 and 4.

From Tables 3, 4, and FIG. 5, it is easily understood that the Δ(−φ)/ΔE corresponds well to the Δθ/ΔE. It implies that the phase shift (0°<−φ<90°) for the intermediate frequencies can be related to the fractional surface coverage (1>θ>0). Also, it implies that the phase-shift profile (−φ vs. E) for the intermediate frequencies corresponds well to the Langmuir adsorption isotherm (θ vs. E) at the interfaces.

D: Determination of the Optimum Intermediate Frequencies

To determine the relation between the phase-shift profile for the intermediate frequencies and the Langmuir adsorption isotherm, a relatively low E is applied to the interfaces as an initial potential. The determination of the optimum intermediate frequencies for the phase-shift profiles at the poly-Ir/0.1 M KOH and 0.1 M H$_2$SO$_4$ electrolyte interfaces is based on the frequency responses shown in FIGS. 6(a) and 10(a), respectively.

Figure 11:
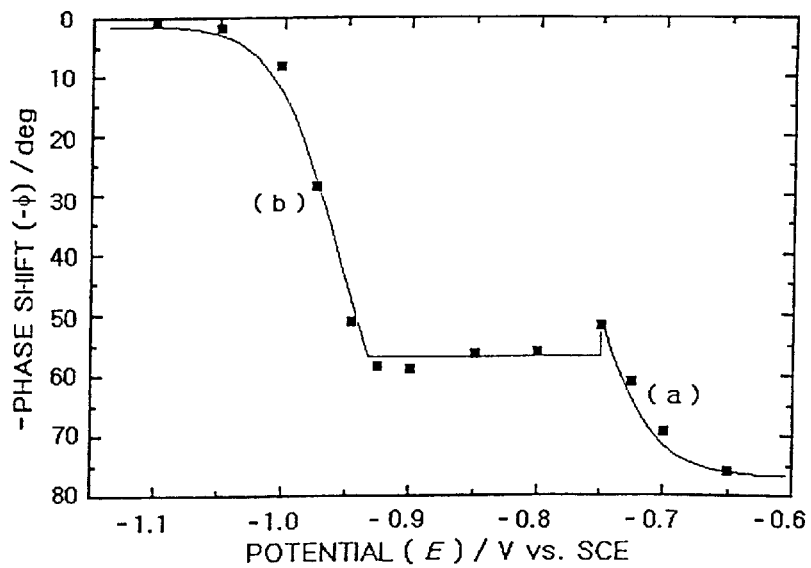
FIG. 11 depicts phase-shift profiles ($-\phi$ vs. E) for ca. 8 Hz at the poly-Ir/0.1 M KOH electrolyte interface. (a) Underpotentially deposited hydrogen region and (b) Overpotentially deposited hydrogen region.
Figure 12:
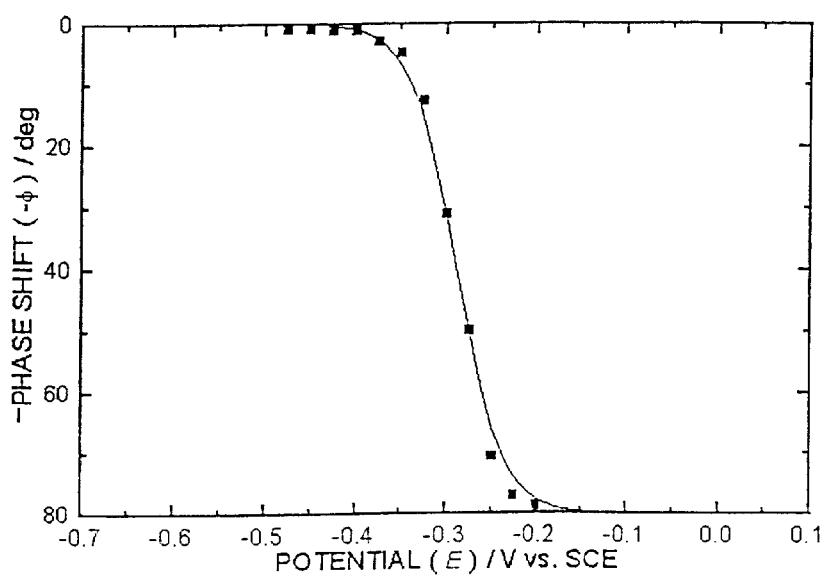
FIG. 12 is a phase-shift profile ($-\phi$ vs. E) for ca. 1 Hz at the poly-Ir/0.1 M $H_2SO_4$ electrolyte interface.

As previously described, the vertical solid line (ca. 8 Hz) shown in FIG. 6(a) is the center frequency of the slope portion of the frequency response curve, i.e., ca. 1–50 Hz. Similarly, the vertical solid line (ca. 1 Hz) shown in FIG. 10(a) is the center frequency of the slope portion of the frequency response curve, i.e., ca. 0.1–10 Hz. Finally, the cathode potentials and the corresponding phase shifts for the intermediate frequencies can be plotted as the $-\phi$ vs. E shown in FIGS. 11 and 12. In FIG. 11, the regions (a) and (b) correspond to the underpotentially deposited hydrogen and the overpotentially deposited hydrogen ranges, respectively. This is discussed in more detail later.

E. Langmuir Adsorption Isotherm

Figure 13:
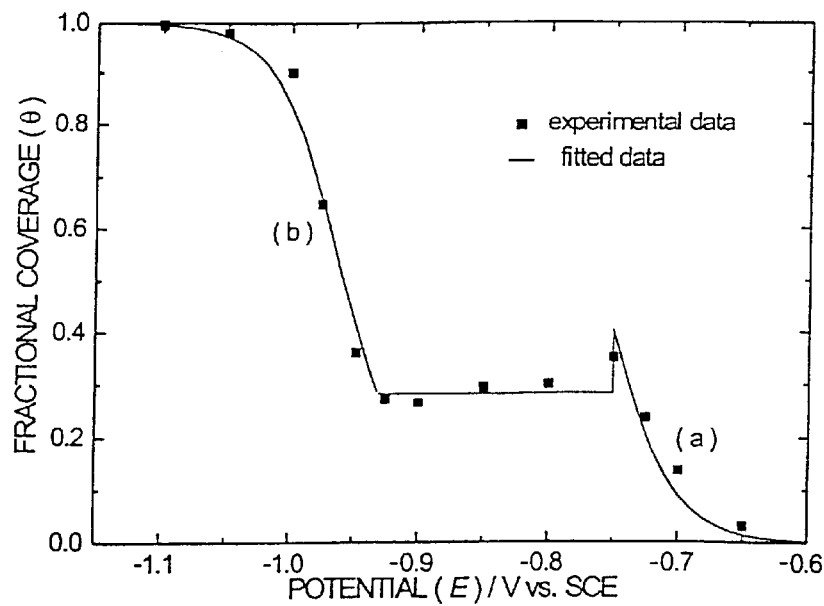
FIG. 13 is a comparison of the experimental and fitted data for the Langmuir adsorption isotherm ($\theta$ vs. E) at the poly-Ir/0.1 M KOH electrolyte interface. (a) $K=7.5\times10^{-1}$ (Underpotentially deposited hydrogen) and (b) $K=3.2\times10^{-4}$ (Overpotentially deposited hydrogen).
Figure 14:
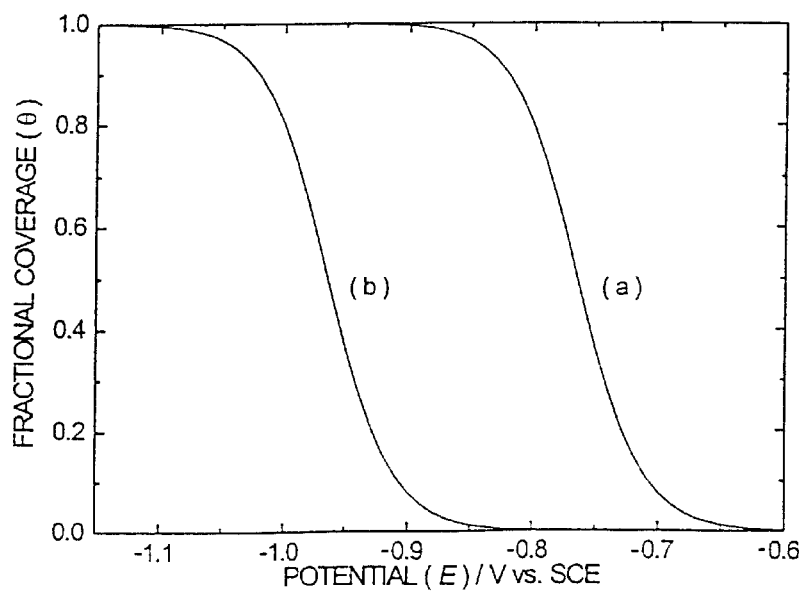
FIG. 14 shows calculated Langmuir adsorption isotherms ($\theta$ vs. E) at the poly-Ir/0.1 M KOH electrolyte interface. (a) $K=7.5\times10-1$ (Underpotentially deposited hydrogen) and (b) $K=3.2\times10^{-4}$ (Overpotentially deposited hydrogen).

At the poly-Ir/0.1 M KOH electrolyte (pH 12.8) interface, the fitted data, i.e., the calculated Langmuir adsorption isotherm ($\theta$ vs. E) using Equation [4], are shown in FIGS. 13 and 14. FIG. 13 also shows the comparison of the experimental and fitted data for the equilibrium constant (K) for H adsorption. FIG. 14 also shows that the $-\phi$ vs. E well corresponds to the $\theta$ vs. E. In FIGS. 11 and 13, it should be noted that the transition region, which is attributed to the underpotentially deposited hydrogen and the overpotentially deposited hydrogen, occurs at ca. $-0.75$ to $-0.93$ V vs. SCE.

By comparing FIG. 11 with FIGS. 13 and 14, it can be easily found that the phase-shift profile ($-\phi$ vs. E) for the intermediate frequency (ca. 8 Hz) is sectionally similar to the Langmuir adsorption isotherm ($\theta$ vs. E). It implies that $K=7.5 \times 10^{-1}$ and $3.2 \times 10^{-4}$ are sectionally applicable to the formation of H, i.e., the underpotentially deposited hydrogen and the overpotentially deposited hydrogen, respectively, at the poly-Ir/0.1 M KOH electrolyte interface. In other words, the poly-Ir surface has the two distinct adsorption sites of the underpotentially deposited hydrogen and the overpotentially deposited hydrogen.

Figure 15:
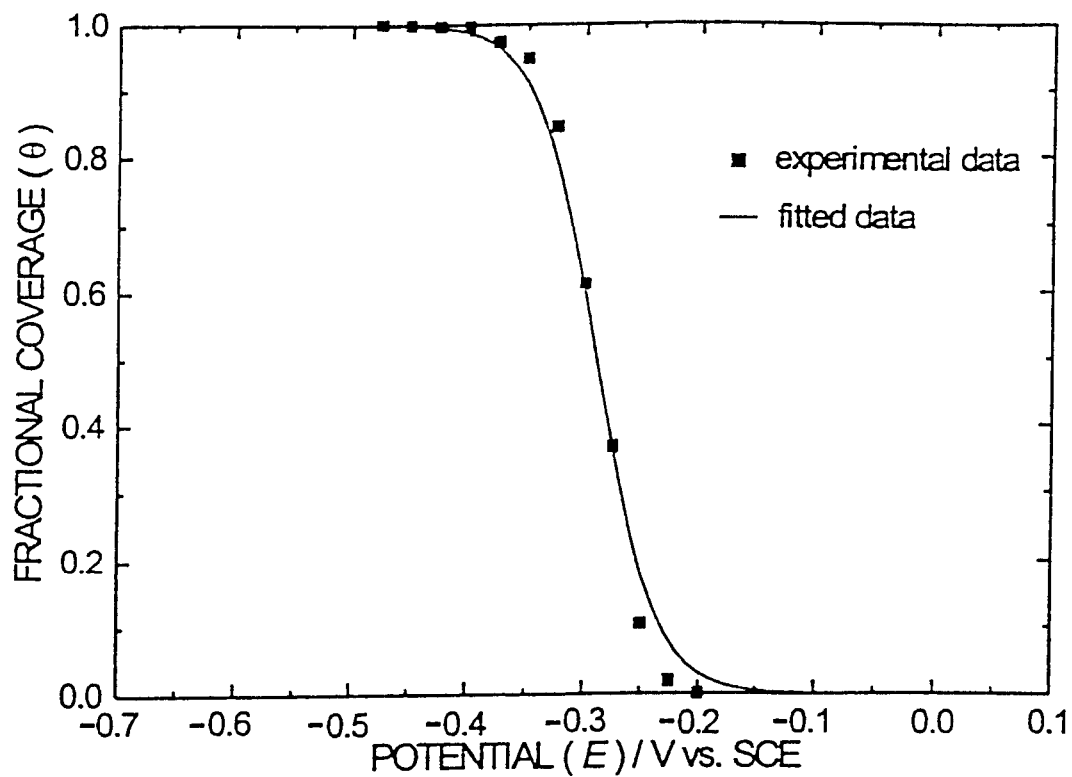
FIG. 15 is a comparison of the experimental and fitted data for the Langmuir adsorption isotherm ($\theta$ vs. E) at the poly-Ir/0.1 M $H_2SO_4$ electrolyte interface. $K=2.0\times10^{-4}$ (Overpotentially deposited hydrogen).

Similarly, at the poly-Ir/0.1 M $H_2SO_4$ electrolyte (pH 1.19) interface, the fitted data, i.e., the calculated Langmuir adsorption isotherm ($\theta$ vs. E) using Equation [4], are shown in FIG. 15. From FIG. 15, it can be easily found that $K=2.0 \times 10^4$ is applicable to the formation of H at the interface. The Langmuir adsorption isotherm is attributed to the overpotentially deposited hydrogen. As expected, the Langmuir adsorption isotherm due to the underpotentially deposited hydrogen has not been observed at the poly-Ir/0.1 M $H_2SO_4$ electrolyte interface. It is understood that the adsorption sites of the underpotentially deposited hydrogen are masked due to a high $H^+$ concentration of the 0.1 M $H_2SO_4$ electrolyte under steady state conditions. However, it should be noted that all the experimental data shown in FIGS. 5, 8–10, 12, 15, and Tables 2 and 4 are beyond the range of the underpotentially deposited hydrogen peak (ca. $-0.185$ V vs. SCE) on the cyclic voltammogram (FIG. 2). The anionic adsorption effect on the underpotentially deposited hydrogen has not been considered.

Under Langmuir adsorption conditions, the relation between the equilibrium constant (K) for H adsorption and the standard free energy ($\Delta G_{ads}$) of H adsorption is given by:

$$2.3RT \log K = -\Delta G_{ads} \quad [5]$$

At the poly-Ir/0.1 M KOH electrolyte interface, it is readily calculated using Equation [5] that $\Delta G_{ads}$ is 0.7 kJ/mol for $K=7.5 \times 10^{-1}$ (underpotentially deposited hydrogen) and 19.9 kJ/mol for $K=3.2 \times 10^{-4}$ (overpotentially deposited hydrogen). It implies that $\Delta G_{ads}$ transits from 0.7 to 19.9 kJ/mol depending on E and vice versa. Consequently, it is understood that the underpotentially deposited hydrogen and the overpotentially deposited hydrogen on the poly-Ir surface act as two distinguishable electroadsorbed H species.

Similarly, at the poly-Ir/0.1 M $H_2SO_4$ electrolyte interface, it is readily calculated using Equation [5] that $\Delta G_{ads}$ is 21.1 kJ/mol for $K=2.0 \times 10^{-4}$ (overpotentially deposited hydrogen).

F. Transition Region

Under the Langmuir adsorption conditions, the transition region shown in FIG. 13 implies that K and $\Delta G_{ads}$ transit depending on the adsorption sites of the electroadsorbed H on the poly-Ir surface. In other words, the poly-Ir has the two distinct adsorption sites of the underpotentially deposited hydrogen and the overpotentially deposited hydrogen corresponding to the two different values of K or $\Delta G_{ads}$.

By comparing FIG. 13 with FIG. 1, it is understood that the transition region (ca. $-0.75$ to $-0.93$ V vs. SCE) on the $\theta$ vs. E curve (FIG. 13) corresponds well to the cathodic and anodic peaks and their valley regions (ca. $-0.75$ to $-0.93$ V vs. SCE) on the cyclic voltammogram (FIG. 1). As previously described, it is attributed to the transition between the two distinct adsorption sites of the underpotentially deposited hydrogen and the overpotentially deposited hydrogen at the poly-Ir/0.1 M KOH electrolyte interface.

The present invention applies to numerous electrochemical systems in which it is desirable to understand electrode kinetics in general and, in particular, the transition between an underpotentially deposited species and an overpotentially deposited species. Such systems include, but are not limited to, fuel cells, batteries, electrochemical polishing/etching, and electrochemical systems for the commercial production of industrial gases. Knowledge of the relation and transition between such species permits the process to be operated in a desired region of either overpotentially deposited or underpotentially deposited species.

The foregoing embodiments and advantages are merely exemplary and are not to be construed as limiting the present invention. The present methods can be readily applied to a wide variety of electrochemical systems. The description of the present invention is intended to be illustrative, and not to limit the scope of the claims. Many alternatives, modifications, and variations will be apparent to those skilled in the art. In particular, although the invention has been described with respect to noble metal/aqueous electrolyte systems, the techniques demonstrated above are equally applicable to other electrode/electrolyte. Such systems include, but are not limited to, platinum, iridium, rhodium, gold, palladium, nickel and electrodes in combination with aqueous electrolytes.

What is claimed is:

1. A method for monitoring electrode electrocatalysis in an electrochemical system comprising:
    performing electrochemical impedance spectroscopy of an electrode/electrolyte system at an intermediate frequency to determine a phase-shift profile;
    modeling the Langmuir adsorption isotherm from the phase-shift profile to determine the region of underpotentially or overpotentially deposited reactive species, wherein the modeling is performed by one of first and second circuits;
    using the Langmuir adsorption isotherm to operate the electrode/electrolyte system in the region of underpotentially or overpotentially deposited reactive species, wherein said first circuit comprises resistors $R_S$ and $R_F$ and capacitor $C_P$ coupled in series, where $R_S$=the electrolyte resistance, $R_F$=the faradaic resistance for the discharge resistance, and $C_P$=the equivalent circuit element of the adsorption pseudocapacitance, and said second circuit comprises a parallel circuit having a capacitance $C_D$ coupled in parallel with resistor $R_F$ and capacitor $C_P$, a resistor $R_P$ coupled in parallel with capacitor $C_P$ and a resistor $R_S$ coupled in series to the parallel circuit, where $C_D$=the double layer capacitance, $R_F$=the faradaic resistance for the discharge resistance, $R_S$=the electrolyte resistance, and $C_P$=the equivalent circuit element of the adsorption pseudocapacitance.

2. A method according to claim 1, wherein the electrode is selected from iridium, platinum, rhodium, gold, palladium, or nickel.

3. A method according to claim 1, wherein the electrolyte is an aqueous electrolyte.

4. A method according to claim 3, wherein the aqueous electrolyte includes KOH.

5. A method according to claim 3, wherein the aqueous electrolyte includes $H_2SO_4$.

6. A method for experimentally determining an adsorption isotherm comprising:

performing electrochemical impedance spectroscopy of an electrode/electrolyte system at an intermediate frequency;

determining values for one of first and second modeling circuits for the impedance spectroscopic data;

using said one of first and second modeling circuits to construct the Langmuir or Frumkin isotherm;

determining the relation and transition of underpotentially and overpotentially deposited reactive species from the constructed Langmuir or Frumkin adsorption isotherm, wherein said first circuit comprises resistors $R_S$ and $R_F$ and capacitor $C_P$ coupled in series, where $R_S$=the electrolyte resistance, $R_F$=the faradaic resistance for the discharge resistance, and $C_P$=the equivalent circuit element of the adsorption pseudocapacitance, and said second circuit comprises a parallel circuit having a capacitance $C_D$ coupled in parallel with resistor $R_F$ and capacitor $C_P$, a resistor $R_P$ coupled in parallel with capacitor $C_P$ and a resistor $R_S$ coupled in series to the parallel circuit, where $C_D$=the double layer capacitance, $R_F$=the faradaic resistance for the discharge resistance, $R_S$=the electrolyte resistance, and $C_P$=the equivalent circuit element of the adsorption pseudocapacitance.

7. A method according to claim 6, wherein the electrode is selected from iridium, platinum, rhodium, gold, palladium, or nickel.

8. A method according to claim 6, wherein the electrolyte is an aqueous electrolyte.

9. A method according to claim 8, wherein the aqueous electrolyte includes KOH.

10. A method according to claim 8, wherein the aqueous electrolyte includes $H_2SO_4$.

11. A method for estimating the phase-shift profile for the optimum intermediate frequency of an electrochemical system comprising:

performing electrochemical impedance spectroscopy of an electrode/electrolyte system;

plotting the frequency response curve of the impedance for the electrode/electrolyte system;

determining the intermediate frequencies for the electrode/electrolyte system from said frequency response curve of the impedance; and modeling the phase-shift profile according to the following equation:

$$\phi = -\tan^{-1}[1/\omega(R_S+R_F)C_P]$$

wherein $\omega$ is the angular frequency;

$R_S$ is the electrolyte resistance;

$R_F$ is the faradaic resistance of the for the discharge reaction; and $C_P$ is the capacitance associated with the adsorption pseudocapacitance.

12. A method according to claim 11, wherein the electrode is selected from iridium, platinum, rhodium, gold, palladium, or nickel.

13. A method according to claim 11, wherein the electrolyte is an aqueous electrolyte.

14. A method according to claim 13, wherein the aqueous electrolyte includes KOH.

15. A method according to claim 13, wherein the aqueous electrolyte includes $H_2SO_4$.

* * * * *